US012569048B2

(12) United States Patent
Gester et al.

(10) Patent No.: US 12,569,048 B2
(45) Date of Patent: Mar. 10, 2026

(54) METHOD FOR REMOVING HAIR FROM AN AREA OF SKIN

(71) Applicant: The Gillette Company LLC, Boston, MA (US)

(72) Inventors: Matthias Gester, Farnborough (GB); Alison Fiona Stephens, Cookham (GB); Martin Stephen Williamson, Bracknell (GB); Ilaria Ambrogio, London (GB); Lara Katharine Goodman, Woking (GB)

(73) Assignee: The Gillette Company LLC, Boston, MA (US)

( * ) Notice: Subject to any disclaimer, the term of this patent is extended or adjusted under 35 U.S.C. 154(b) by 182 days.

(21) Appl. No.: 18/383,079

(22) Filed: Oct. 24, 2023

(65) Prior Publication Data

US 2024/0156232 A1 May 16, 2024

(30) Foreign Application Priority Data

Oct. 26, 2022 (EP) .................................... 22203961

(51) Int. Cl.
| | |
|---|---|
| *A45D 26/00* | (2006.01) |
| *A61K 8/31* | (2006.01) |
| *A61K 8/37* | (2006.01) |
| *A61K 8/891* | (2006.01) |
| *A61K 8/898* | (2006.01) |
| *A61Q 9/02* | (2006.01) |

(52) U.S. Cl.
CPC ............ *A45D 26/0028* (2013.01); *A61K 8/31* (2013.01); *A61K 8/37* (2013.01); *A61K 8/891* (2013.01); *A61K 8/898* (2013.01); *A61Q 9/02* (2013.01)

(58) Field of Classification Search
None
See application file for complete search history.

(56) References Cited

U.S. PATENT DOCUMENTS

| | | | |
|---|---|---|---|
| 2,342,558 A | 2/1944 | Schjotz | |
| 5,849,281 A | 12/1998 | Babinski et al. | |
| 6,024,951 A | 2/2000 | Babinski et al. | |
| 2006/0002878 A1* | 1/2006 | Acher | B65D 75/5855 424/73 |
| 2007/0110703 A1 | 5/2007 | Ogrady et al. | |
| 2013/0046256 A1* | 2/2013 | Smith | A61Q 9/04 604/289 |
| 2014/0100589 A1 | 4/2014 | Gordon et al. | |
| 2022/0330983 A1 | 10/2022 | Kearney et al. | |

OTHER PUBLICATIONS

All Office Actions; U.S. Appl. No. 18/383,083, filed Oct. 24, 2023.
(Continued)

*Primary Examiner* — Todd J Scherbel
(74) *Attorney, Agent, or Firm* — Andrés E. Velarde

(57) ABSTRACT

The present invention refers to a method for removing hair from an area of skin by applying a shaving aid composition to the area of skin to be shaved. The shaving aid composition includes water, at least one oil and at least one shear thinning structurant. The area of skin is shaved using a hair removal device comprising a treatment sheet with aperture blades.

14 Claims, 7 Drawing Sheets

(56)     References Cited

OTHER PUBLICATIONS

"Fast Absorbing Moisturiser", in Database GNPD Mintel, Mar. 3, 2022, 9 Pages.
EP Extended EP Search Report and Opinion for 22203961.2 dated Apr. 12, 2023, 8 pages.
Unpublished U.S. Appl. No. 18/383,083, filed Oct. 24, 2023, to Matthias Gester.
Extended EP Search Report and Search Opinion for 23205385.0 dated Mar. 15, 2024, 10 pages.
PCT Search Report and Written Opinion for PCT/US2023/077567 dated Feb. 21, 2024, 12 pages.

* cited by examiner

40

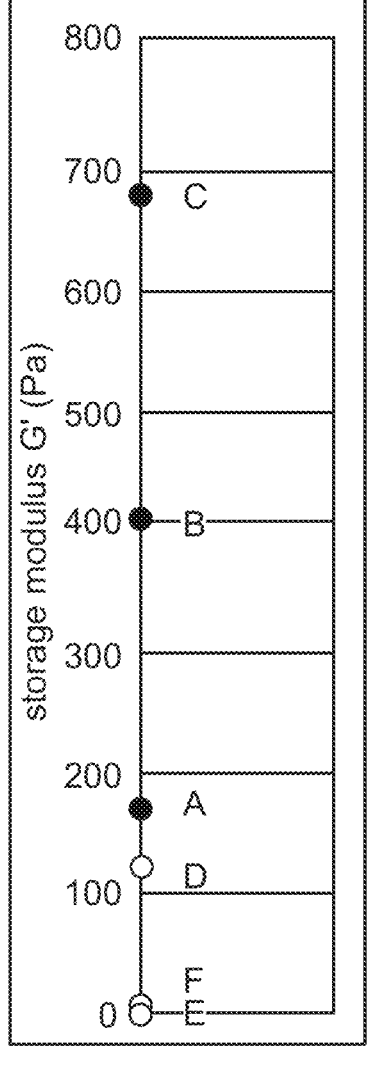
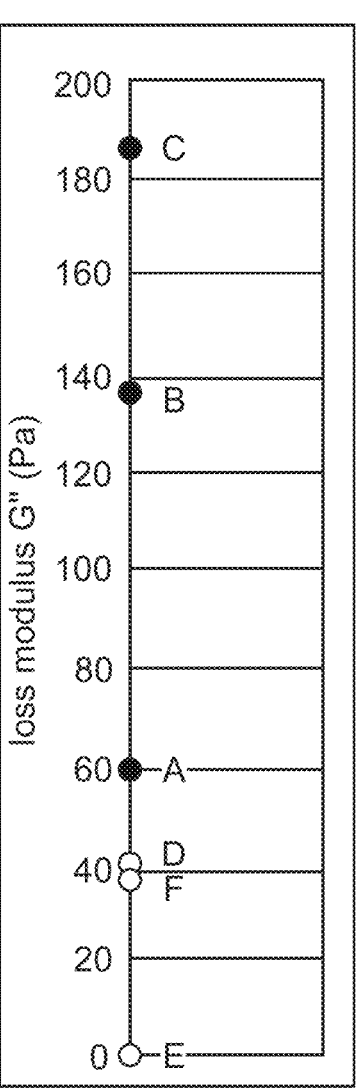
● preferred          ○ unsuitable
Fig. 7a                    Fig. 7b

METHOD FOR REMOVING HAIR FROM AN AREA OF SKIN

FIELD OF THE INVENTION

The present invention refers to a method for removing hair from an area of skin comprising the step of applying a shaving aid composition to the area of skin to be shaved, the shaving aid composition comprising water, at least one oil and at least one shear thinning structurant and shaving the area of skin to be shaved using a hair removal device comprising a treatment sheet with aperture blades.

BACKGROUND OF THE INVENTION

Conventional hair removal devices that contain a plurality of straight linear blades oriented orthogonal to the handle axis can only be used in a safe method for removing body hair when pulled or pushed across the skin in one linear direction perpendicular to the blades and parallel to the handle axis. Such razors are for example known from US 2010/0319198 A1. When using such a shaving razor in other directions the cutting edges may slice into the skin.

The plurality of straight linear blades in conventional shaving razors are typically oriented at a clearance angle (the angle between the clearance face and the contacting surface to the skin) of about 200 with respect to the skin surface to be shaved. These shave razors produce a very close shave, where the hairs are cut close to skin level. However, placing exposed blade edges at an angle in close contact with the skin can result in nicks and cuts to the skin and therefore skin irritation when the skin bulges into the gaps between the blades.

Skin irritation may be reduced by applying a liquid shaving aid onto the skin prior to removing hair with the hair removal device. This shaving aid fluid forms a liquid film between the blade edge and the skin to protect the skin from direct contact and it lubricates the skin which reduces the skin bulging into the gaps between the blades.

Furthermore, the contact area of these angled straight blades with the skin is extremely small causing very high pressure between the blade tip and skin, thus resulting in high shear rates in the thin fluid layer of shaving aid. In consequence, special shaving aids are required that maintain sufficient lubrication and protection under these conditions. For this purpose, shaving foams, gels and soaps are typically used with bladed razors. Such shaving aid composition are for example known from US 2015/0121705 A1 and US 2007/0137042 A1.

Many razor cartridges include skin engaging members, commonly referred to as lubrication strips. These lubrication strips are typically located behind the blades so that, as a user performs a shave stroke, the skin comes in contact with the blades prior to coming in contact with the skin engaging member. Many different types of skin engaging members have been disclosed. See e.g., U.S. Pat. No. 6,301,785 B1, US 2009/0223057 A1, and US 2008/060201 A1. Some lubrication strips contain one or more types of polyethylene oxide (PEO) with water insoluble polymers such as polystyrene.

An alternative option is the use of treatment sheets. When using treatment sheets as hair removal devices, the treatment sheets comprise a plurality of aperture blades that comprise cutting edges along at least a portion of the inner perimeter of each aperture. The aperture blades can be used in any direction resulting in a more efficient shaving.

Treatment sheets aim to deliver both a close shave and an irritation free shave by placing a blade parallel to the skin. The clearance angle of an aperture blade is 0 degree with respect to the skin surface making the shaving very safe. Furthermore, the skin bulge is significantly reduced by forming the cutting edges along the internal perimeter of a plurality of aperture blades, which are surrounded by a solid substrate material that supports the skin and prevents skin bulging into the apertures.

The skin safety and hair removal efficiency resulting from the use of a treatment sheet containing a plurality of enclosed cutting edges is determined by the dimensions of the enclosed cutting edges, referred to herein as the aperture blades, the amount of skin sup-port provided by the solid substrate material, the overall size of the treatment sheet and the clearance angle of the aperture blades with respect to the skin surface.

The hair removal efficiency is determined by the total cutting edge length of the treatment sheet, which can be determined by summing the cutting edge lengths of all of the aperture blades on the treatment sheet whereby the cutting length of an aperture blade is the portion of the length of perimeter within the apertures that comprises a cutting edge. This total cutting length should be maximized to increase the cutting efficiency.

The safety of the shave is determined by the area of contact between the skin and the solid substrate material of the treatment sheet. For a safe shave, the area of contact between the skin and the substrate of the treatment sheet should be maximized.

The overall performance if the treatment sheet is affected by the transparency. The solid substrate material of the treatment sheet maintains contact with the skin during use and prevents excessive skin bulging into the apertures thus resulting in a safe shave. When the transparency of the treatment sheet is high, the skin is not sufficiently supported and is able to bulge into the apertures resulting in skin damage and irritation. When the transparency is low, only few or small aperture blades are present, which results in a low total cutting length and an inefficient shave.

When using treatment sheets as hair removal device the following requirements must be fulfilled:

a greater area of solid material in contact with the skin,
the cutting edges have to be oriented at low clearance angle,
less pressure during use on the skin, and
continuous change of the direction of movement over the skin.

For a method of using the above treatment sheet a shaving aid is required that is tailored to the properties of the treatment sheet and a different kind of shaving aid is required.

It was therefore the object of the present invention to provide a method for removing hair from an area of skin with a good balance between safety and hair removal efficiency using a treatment sheet and a tailored shaving aid that supports the safety and efficiency of the hair removal device comprising a treatment sheet.

SUMMARY OF THE INVENTION

This object is solved by the method for removing hair from an area of skin with the fea-tures of claim 1. The further dependent claims refer to preferred embodiments of the invention.

The present invention refers to a method for removing hair from an area of skin comprising the step of applying a shaving aid composition to the area of skin to be shaved, the shaving aid composition comprising water, at least one oil and at least one shear thinning structurant and shaving the area of skin to be shaved using a hair removal device comprising a treatment sheet with aperture blades.

Terms and Definitions

The term "comprising" in the claims and in the description of this application has the meaning that further components are not excluded. Within the scope of the present invention, the term "consisting of" should be understood as preferred embodiment of the term "comprising". If it is defined that a group "comprises" at least a specific number of components, this should also be understood such that a group is disclosed which "consists" preferably of these components.

The following definitions are used for describing the present invention:

Treatment Sheet

The term "treatment sheet" in the personal care product of the present invention refers to a sheet comprising a plurality n of apertures. The periphery or perimeter of the apertures comprise cutting edges, used for removing hair and exfoliation or other treatments on skin.

The treatment sheet is desirably flat. A "flat" material generally has planar surfaces without protrusions or indentations. As used herein, "flat" and "planar" can be used in-terchangeably.

Total Aperture Area A

The treatment sheet comprises a number n of apertures, each with an aperture area $\alpha_i$ (i=1 to n) on the skin contacting surface. The summation of all the aperture areas $\alpha_i$ for all n apertures results in the total aperture area A which is calculated according to the formula:

$$A = \Sigma_{i=1}{}^n \alpha_i, i = 1 \text{ to } n$$

Total Cutting Length L

The treatment sheet comprises a number n of apertures, each with an aperture cutting length $l_i$, which corresponds to the length of the portion of the perimeter of an aperture that comprises a cutting edge. The summation of all the aperture cutting length $l_i$, for all n apertures results in the total cutting length L which is calculated according to the formula:

$$L = \Sigma_{i=1}{}^n l_i = 1 \text{ to } n$$

Total Cutting Zone Area S

The treatment sheet is surrounded by a frame member. The area of the treatment sheet that is enclosed by this frame member and not covered by the frame member is the cutting zone area S.

Area of Contact C

The area of contact is the solid material area of the treatment sheet which is in contact with the skin and is defined by the following formula:

$$C = S - A$$

Transparency T

The transparency T of a treatment sheet is defined as the ratio of the total aperture area A divided by the cutting zone area S.

$$T = \frac{A}{S}$$

Clearance Face and Clearance Angle

The clearance face is the surface of a cutting blade that passes over the skin; the angle between the clearance face and the skin surface is the clearance angle $\alpha$.

Rake Face

The rake face is the surface of a cutting blade over which the hair ends slide that have been removed in the cutting process. The cutting bevel of a cutting blade is enclosed by the rake face and the clearance face and denoted by the bevel angle $\theta$.

DESCRIPTION OF THE INVENTION (A) According to the present invention a method for removing hair from an area of skin comprising the steps of: applying a shaving aid composition to the area of skin to be shaved, the shaving aid composition comprising water, at least one oil and at least one shear thinning structurant, wherein the shaving aid composition has a polar component of surface free energy of 30 to 80 mJ/m$^2$, (B) shaving the area of skin to be shaved using a hair removal device (10) comprising a planar treatment sheet (40) with a plurality of aperture blades (430).

Shaving Aid Composition and its Physical Properties

Regarding the shaving aid composition, the composition must provide sufficient lubrication with little drag to enable movement of the hair removal device with rather large contact area in every direction parallel to the skin to the skin without stick slip. Moreover, the shaving aid composition should provide a cushioning effect on the skin which reduces or eliminates the feel of cutting edges (scraping) on the skin. As a further aspect, the shaving aid composition should show a chemical stability over an extended duration of use (up to 5 min) without the fluid changing through evaporation or skin penetration of ingredients. Furthermore, it is preferred that the shaving aid composition is rinsable after use.

According to a preferred embodiment, the shaving aid composition has a polar component of surface free energy (SFE) of 40 to 60 mJ/m$^2$. Due to the very low-polar shaver surface components (PTFE coated treatment sheet and metallic frame member) with $\gamma^P < 3$ mJ/m$^2$ and on skin with $\gamma^P < 8$ mJ/m$^2$ this results in:

High surface tension (blade: >30 mJ/m$^2$, skin: >15 mJ/m$^2$)

Large contact angle (treatment sheet: >100°, skin: >80°)

This leads to the formation of fluid droplets between the shaver and skin surface, which provide two functions:

A ball bearing-like lubrication mechanism

A cushioning layer of the shaving aid composition between the 2 surfaces

This effect is enhanced by the presence of water, which has a comparably polar SFE component ($\gamma^P < 50$ mJ/m$^2$) to the preferred shaving aids, making it energetically favorable for the shaving aid to bond to any residual water.

According to another preferred embodiment, the shaving aid composition has a contact angle on the surface of the treatment sheet of 100 to 180°, more preferably 110 to 150°.

Surface Energy, Contact Angle and its Measurement

Surface energy (SFE) defines how a material will wet, spread and adhere onto another surface. SFE is often broken into two components, the dispersive (or sometimes referred to as nonpolar) and the polar component. The dispersive component describes the van der Waals type interactions available on a surface. All surfaces have van der Waals interactions and these interactions typically increase with higher molecular weight compounds. The polar component describes the molecular groups that are available to interact via polar interactions, for example, hydrogen bonding, dipole-dipole or Lewis-Acid/Lewis base interactions. A surface with a high polar component is more hydrophilic than a surface with little to no polar component.

The surface tension of high viscosity fluids, having a viscosity greater than 5 Pascal seconds at a shear rate of 1 second$^{-1}$, was determined from thin films of these materials. Thin films were evaluated immediately after spreading onto a microscope glass slide. The personal care product components (frame member and treatment sheet) were measured as a solid material. Contact angle analysis was used to determine the surface energy of solids or thin films of very viscous liquids following ASTM D7334-08 using videos recorded at 200 frames per second for 5 seconds. Water and diiodomethane were dispensed onto thin films of high viscosity fluids or samples of solid materials and wetting of the resulting droplets was captured in profile. First Ten Angstrom software (Version 2.1, build 378) was used to extract contact angles from the videos. Fowkes equation of state was used to convert contact angles into surface energy components.

Total surface tension of low viscosity samples of shaving aid, having a viscosity of equal or less than 5 Pascal seconds at a shear rate of 1 second$^{-1}$, was determined using the Wilhelmy plate technique following ASTM D1331-20 Method C. The nonpolar (dispersive) component of the surface energy was derived from the wetting properties on Teflon following ASTM D7334-08 except the solvent used is a sample of the shaving aid fluids. Images of the droplets on the Teflon surface were captured and First Ten Angstrom software (Version 2.1, build 378) was used to extract contact angles from the images. The dispersive component of surface tension is deduced using the primary Fowkes equation of state whereby the polar SFE component of the Teflon is assumed to be zero mJ/m$^2$. The polar component of the liquid was calculated by subtracting the dispersive component from the total surface free energy.

Surface tension was measured with the Kruss K-100 instrument and contact angle were measured using the FTA Model 200 dynamic contact angle analyzer.

According to another preferred embodiment, the shaving aid composition has a storage modulus G' of 150 to 1500 Pa, more preferably of 250 to 1000 Pa.

According to another preferred embodiment, the shaving aid composition has a loss modulus G" of 50 to 500 Pa, more preferably of 100 to 200 Pa.

Regarding rheology, preferred shaving aid compositions according to the present invention show a shear dependent viscosity that decreases with increasing shear rate, i.e., exhibit shear thinning viscous flow.

Storage and loss modulus are measures of the respective abilities for the shaving aid to store energy through elastic deformation or dissipate energy through viscous flow when the fluid is moved and squeezed between the treatment sheet and the skin while the hair removal device is moved in multiple direction over the skin.

Rheology and its Measurement

Oscillation frequency sweeps provide insight into the viscoelastic properties of the fluids. The oscillatory frequency sweep involves applying small, sinusoidal (clockwise then counterclockwise) strains to a sample, sweeping the frequency of oscillation and monitoring the resulting stress response, from which viscoelastic information can be gained. The test is used to identify the relative proportions of viscous or elastic behavior across a range of deformation timescales that is expressed as the storage (G') and loss modulus (G") versus frequency. Storage and loss modulus are measures of the respective abilities for the material to store energy through elastic deformation or dissipate energy through viscous flow during each oscillatory deformation cycle.

Oscillation Frequency Sweeps were carried out following a 60 second equilibration time at 20° C. the samples were exposed to oscillatory frequency sweeps, 100 rad/second to 0.1 rad/second at 0.1% oscillation strain. Testing was performed on a research rheometer (DHR2, TA Instruments) fitted with a 40 mm crosshatched advanced Peltier plate measuring system, test gap set to 500 μm. A solvent trap cover was employed to minimize drying of the sample at the exposed geometry edge.

Shaving Aid Composition and its Chemical Composition

The shaving aid composition of the present invention contains at least one oil, at least one shear thinning structurant, at least one additive, and water Oil The shaving aid composition may comprise at least one oil to form an oil-in-water emulsion or a water-in-oil-in-water emulsion. Oils may be used to solubilize, disperse, or carry materials that are not suitable for water- or water-soluble solvents. Oils may be fluid at room temperature. The oils may be volatile or nonvolatile. "Nonvolatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 20° C. Volatile oils may be used to provide a lighter feel when a heavy, greasy film is undesirable. Suitable oils include hydrocarbons, esters, amides, ethers, silicones, and mixtures thereof.

It is preferred, that the at least one oil is selected from the group consisting of:

hydrocarbons, preferably straight, branched, or cyclic alkanes and alkenes having 20 to 65 carbon atoms, esters, preferably esters from fatty acids or alcohols, amides, preferably N-acetyl-N-butylaminiopropionate, isopropyl N-lauroylsarcosinate, butylphthalide, isopropylphthahmide, and N,N,-diethyltoluamide, ethers, preferably saturated aid unsaturated fatty ethers of a polyhydric alcohol, and alkoxylated derivatives thereof, silicones, preferably polysiloxanes and mixtures thereof.

Suitable hydrocarbon oils include straight, branched, or cyclic alkanes aid alkenes. The chain length may be selected based on desired functional characteristics such as volatility. Suitable volatile hydrocarbons may have between 5-20 carbon atoms or, alternately, between 8-16 carbon atoms.

Other suitable oils include esters. These esters include esters with hydrocarbyl chains derived from fatty acids or alcohols (e.g., monoesters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.) Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, butyloctyl salicylate, phenylethyl benzoate, dicaprylyl carbonate, dioctyl runagate, dicaprylyl maleate, isononyl isononanoate, propylene glycol dicaprate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters." Other esters suitable for use in the personal care composition include those known as polyhydric alcohol esters and glycerides.

Other suitable oils include amides. Amides include compounds having an amide functional group while being liquid at 25° C. and insoluble in water. Suitable amides include, but are not limited to, N-acetyl-N-butylaminiopropionate, isopropyl N-lauroylsarcosinate, butylphthalimide, isopropylphthalimide, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include, but are not limited to, $C_{4-20}$; alkyl ethers of polypropylene glycols, and di-$C_8$-alkyl ethers. Suitable examples of these materials include PPG-14 butyl ether, PPG-15 stearyl ether, PPG-11 stearyl ether, dioctyl ether, dodecyl octyl ether, and mixtures thereof.

Suitable silicone oils include polysiloxanes. Polylsiloxanes may have a viscosity of from about 0.5 to about 1,000.000 centistokes at 25° C. Such polysiloxanes can be represented by the general chemical formula:

$$R_3SiO[R_2SiO]_xSiR_3$$

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular, in certain embodiments, R is hydrogen, methyl, or ethyl. Commercially available polysiloxanes include the polydimethylsiloxanes, which are also known as dimethicones, examples of which include the DM-Fluid Series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100, 000, and 300,000 centistokes. Suitable dimethicones include those represented by the chemical formula:

$$R_3SiO[R_2SiO]_x[RR'SiO]_ySiR_3$$

wherein R and R' are each independently hydrogen or $C_{1-30}$ straight or branched chain, saturated or unsaturated alkyl, aryl, or trialkylsiloxy and x and y are each integers of 1 to 1,000,000 selected to achieve the desired molecular weight. Suitable silicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone, is available as s 2502 Cosmetic Fluid from Dow Corning or as Abil Wax 9801 or 9814 from Evonik Goldschinidt GmbH.

Cyclic silicones are one type of silicone oil that may be used in the shaving aid composition. Such silicones have the general formula:

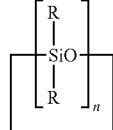

wherein R is independently selected from hydrogen or $C_{1-30}$ straight or branched chain, saturated or unsaturated alkyl, phenyl or aryl, trialkylsiloxy; and where n=3-8 and mixtures thereof. Commonly, a mixture of cyclomethicones is used where n is 4, 5, and/or 6. Commercially available cyclomethicones include Dow Corning UP-1001. Ultra Pure Fluid (i.e. n=4), Dow Corning XIAMETER® PMX-0245 (i.e. n=5), Dow Corning XIMAMETER® PMX-0245 (i.e. n=6), Dow Corning 245 fluid (i.e. n=4 and 5), and Dow Corning 345 fluid (i.e. n=4, 5, and 6).

Quaternary silicones are another type of silicone oils that may be used, in the shaving aid composition. Quaternary silicones may be comprised of at least one silicone block and at least one non-silicone block containing quaternary nitrogen groups, wherein the number of the non-silicone blocks is one greater than the number of the silicone blocks. The concentration level of the oil phase ingredients either singularly or collectively may range from 2% to less than 15% by weight of the base composition. Some preferred concentration levels include from about 2% to about 12%, and from about 5% to about 14%, by weight of the base composition.

Shear Thinning Structurant

According to a preferred embodiment, the at least one shear thinning structurant is selected from the group consisting of clays and gums, microgels, super absorbent polymers, gel networks formed from fatty amphiphiles and mixtures thereof.

As used herein the terms 'microgels' refers to crosslinked polymeric entities which swell and bind water in order to make a fluid more stable and create shear thinning properties. They can be provided in solid or liquid forms. Preferred polymers include but are not limited to: Polyacrylamide, Hydroxyethyl Acrylate/Sodium Acryloyldimethyltaurate Copolymer, Sodium Acrylate/Sodium Acryloyldimethyltaurate Copolymer, Ammonium Polyacrylate, Sodium Acrylate/Acryloyldimethyltaurate/Dimethylacrylamide Crosspolymer, Hydroxyethyl Acrylate/Sodium Acryloyldimethyltaurate Copolymer which can be purchased from Seppic or Carboxylic Acid Polymers (Carbomers) such as Ultrez 10, Carbopol 934, Carbopol 980 and ETD 2050 which can be purchased from Lubrizol or Ammonium Acryloyldimethyltaurate/VP Copolymer, Sodium Acryloyldimethyltaurate/VP Copolymer, Ammonium Acryloyldimethyltaurate/Beheneth-25 Methacrylate Crosspolymer, which can be purchased from Clariant. The most preferred electrolyte sensitive polymer is Polyacrylamide available as Sepigel 305 (Polyacrylamide & C13-14 Isoparaffin & Laureth-7).

The term "superabsorbent polymer" is understood to mean a polymer which is capable, in its dry state, of spontaneously absorbing at least 20 times its own weight of aqueous fluid, in particular of water and especially of distilled water. Such superabsorbent polymers are described in the work "Absorbent Polymer Technology, Studies in Polymer Science 8" by L. Brannon-Pappas and R. Harland, published by Elsevier, 1990.

These polymers have a high capacity for absorbing and retaining water and aqueous fluids. After absorption of the aqueous liquid, the particles of the polymer thus impregnated with aqueous fluid remain insoluble in the aqueous fluid and thus retain their separated particulate state.

The superabsorbent polymer used in the composition of the invention is preferably provided in the form of particles which, once hydrated, swell with the formation of soft beads having a number-average diameter of 10 μm to 1000 μm.

The superabsorbent polymers used in the present invention are preferably crosslinked acrylic homo- or copolymers which are preferably neutralized, and which are provided in the particulate form.

Mention may in particular be made of the polymers chosen from: crosslinked sodium polyacrylates, such as, for example, those sold under the names Octacare X100, X110 and RM100 by Avecia, those sold under the names Flocare GB300 and Flosorb 500 by SNF, those sold under the names Luquasorb 1003, Luquasorb 1010, Luquasorb 1280 and Luquasorb 1100 by BASF, those sold under the names Water Lock G400 and G430 (INCI name: Acrylamide/Sodium Acrylate Copolymer) by Grain Processing, or Aqua Keep 10 SH NF, Aqua Keep 10 SH NFC, sodium acrylate crosspolymer-2, provided by Sumitomo Seika, starches grafted by an acrylic polymer (homopolymer or copolymer) and in particular by sodium polyacrylate, such as those sold under the names Sanfresh ST-100C, ST100MC and IM-300MC by Sanyo Chemical Industries (MCI name: Sodium Polyacrylate Starch), hydrolysed starches grafted by an acrylic polymer (homopolymer or copolymer), in particular the actyloacrylamide/sodium acrylate copolymer, such as those sold under the names Water Lock A-240, A-180, B-204, D-223, A-100, C-200 and D-223 by Grain Processing (NCI name: Starch/Acrylamide/Sodium Acrylate Copolymer).

Preferably, the superabsorbent polymer is a sodium polyacrylate starch that in its non-swollen state exhibits a number-average size of less than or equal to 100 μm, preferably of less than or equal to 50 μm, for example ranging from 2 μm to 100 μm, with a median particle size of 25, or preferably in the range of about 2 μm to about 40 μm with a median particle size of 12. The viscosity of a solution in 1% water is preferably in the range of to 30 Pas, even more preferably 22 to 29 Pas, at a pH of 4, and in the range of 23 to 28 Pas, at a pH of 7. Preferred superabsorbent polymers include Makimousse 12 and Makimouse 25 supplied by Kobo Products Inc.

The superabsorbent polymer can be present in the composition of the invention in a content as active material ranging, for example, from 0.01 to 10% by weight, preferably from 0.05 to 6% by weight, preferably from 0.1 to 4% by weight, preferentially from 0.1 to 3% by weight, indeed even from 0.1 to 2% by weight, with respect to the total weight of the composition.

As used herein, the term "gel network" refers to a lamellar or vesicular solid crystalline phase which comprises at least one fatty amphiphile. Gel networks have been used for years in cosmetic creams and hair conditioners. Gel networks are a re-solidified liquid crystal gel phase formed by fatty amphiphiles (e.g., cetyl air stearyl alcohol) and a hydrophilic phase (e.g. water). It is formed by undergoing a melting and then re-solidification process in the hydrophilic phase. The gel network will typically have a lower thermal transition than the melt temperature of the fatty amphiphile itself.

The gel networks in this invention may comprise one or more fatty alcohols. Fatty alcohols typically include monohydric alcohols having 8-22 carbon atoms although longer chain alcohols in excess of 30 carbons may be used. The fatty alcohols may be saturated or unsaturated. The fatty alcohols may be straight or branched, in particular, the phase may comprise straight chain, saturated fatty alcohol with a terminal hydroxyl. Suitable fatty alcohols include decyl alcohol, laurel alcohol, myristyl alcohol, cetyl alcohol, stearyl alcohol, isostearyl alcohol, cetearyl alcohol, icosyl alcohol, behenyl alcohol. The phase may comprise from about 0.1%, 0.5%, 1%, 1.5%, 2%, 3%, 5% to about 5%, 7.5%, 10% 15% 20%, by weight of the composition, of fatty alcohol.

The shaving aid composition of the present invention may contain one or more shear thinning structurant, from about 01% to about 5%, alternatively from about 01% to about 4%, alternatively from, about 0.25% to about 3%, by weight of the composition.

Additive

Preferably, the at least one additive is selected from the group consisting of emulsifiers, skin care actives (in particular vitamins, peptides and peptide derivatives, sugar amines), moisturizing agents, conditioning agents, exfoliating agents, antimicrobial agents, antidandruff agents, skin lightening agents (sunless) tanning agents, perfumes, preservatives, chelants, sensates, desquamation actives, antiacne actives, topical anaesthetics, tanning actives, antimicrobial actives, sunscreen actives, visual skin enhancers minerals, opacifiers, anti-inflammatories, antioxidants, minerals, anti-inflammatories, antioxidants, humectants, particles and mixtures thereof.

In general, the shaving aid composition can contain one of the following additives:

Emulsifier

The shave care composition of the present invention contains one or more emulsifying agents, from about 0.1% to about 20%, alternatively from about 0.5% to about 15%, alternatively from about 1.0% to about 12%, by weight of the composition.

Nonlimiting examples of surfactants for emulsification for use in the compositions of the present invention are disclosed in McCutcheon's, Detergents and Emulsifiers, North American edition (1986), published by allured Publishing Corporation; and McCutcheon's, Functional Materials, North American Edition (1992). Preferred emulsifiers are nonionic surfactants/emulsifiers. Nonlimiting useful emulsifiers herein include those selected from the group consisting of alkyl glucosides, alkyl polyglucosides, polyhydroxy fatly acid amides, alkoxylated fatty acid esters, sucrose esters, alkoxylated fatty alcohols, amine oxides, and mixtures thereof. Most preferred are alkoxylated fatty alcohols and alkyl glucosides and mixtures thereof. Other surfactants include anionic and amphoteric surfactants and mixtures thereof. Anionic surfactants include sarcosinates, sulfates, sulfonate, isethionate, taurates, phosphates, lactylates, glutamates, soaps, such as the sodium, potassium and lower alkanolamine (preferably triethanolamine salts of C12-22, preferably C14-18, fatty acids. Typical fatly acids include lauric, myristic, palmitic and stearic acid and mixtures thereof. The preferred fatty acids are palmitic and stearic.

Humectants

The compositions of the present invention may include one or more humectants. The composition of the present invention may comprise from about 1% to about 30%; alternatively, from about 2% to about 20%; or, alternately, from about 3% to about 15% of the humectant, when present. An exemplary class of humectants polyhydric alcohols. Suitable polyhydric alcohols include polyalkylene glycols and alkylene polyols and their derivatives, including propylene glycol, dipropylene glycol, polypropylene glycol, polyethylene glycol and derivatives thereof; sorbitol; hydroxypropyl sorbitol; erythritol; threitol; pentaerythritol xylitol; glucitol; mannitol; hexylene glycol; butylene glycol (e.g., 1,3-butylene glycol), pentylene glycol, hexane triol 1,2,6-hexanetriol); glycerine, ethoxylated glycerine; and propoxylated glycerine.

Other suitable humectants include sodium 2-pyrrolidone-5-carboxylate, guanidine; glycolic acid and glycolate salts (e.g., ammonium and quaternary alkyl ammonium), lactic acid and lactate salts (e.g., ammonium and quaternary alkyl ammonium); aloe vera, in any of its variety of forms (e.g., aloe vera gel); hyaluronic acid and derivatives thereof (e.g., salt derivatives such as sodium hyaluronate); lactamide monoethanolamine; acetamide monoethanolamine; urea; panthenol; sodium pyroglutamate (NaPCA), water-soluble glyceryl poly(meth)acrylate lubricants (such as Hispagel®) and mixtures thereof.

Particles

The compositions of the present invention mar comprise from about 0001% to about 40%, alternatively from about 1% to about 30%, and alternatively from about 2% to about 20%, of one or more particulate materials and/or cosmetic powders. Non-limiting examples of suitable powders include inorganic powders (for example, iron oxides, titanium dioxides, zinc oxides, silica), organic powders, composite powders, optical brightener particles, and mixtures of any of the foregoing. These particulates can, for instance, be platelet shaped, spherical, elongated or needle-shaped, or irregularly shaped; surface coated or uncoated; porous or non-porous; charged or uncharged; and can be added to the current compositions as a powder or as a pre-dispersion. In one embodiment, the particulate material is hydrophobically coated.

Suitable organic powders particulate materials include, but are not limited, to polymeric particles chosen from the methylsilsesquioxane resin microspheres, for example, Tospearl™ 145A, (Toshiba Silicone); microspheres of polymethylmethacrylates, for example, Micropearl™ M 100 (Seppic); the spherical particles of crosslinked polydimethylsiloxanes, for example, Trefil™ E 506C or Trefil™ E 505C (Dow Corning Toray Silicone); spherical particles of polyamide, for example, nylon-12, and Orgasol™ 2002D Nat C05 (Atochem); polystyrene microspheres, for example Dyno Particles, sold under the name Dynospheres™, and ethylene acrylate copolymer, sold under the name Flo-Bead™ EA209 (Kobo); aluminium starch octenylsuccinate, for example Dry Flo™ (Akzo Nobel); polymethyl silsesquioxane coated tapioca particles, for example Dry Flo TS™ (Akzo Nobel); microspheres of polyethylene, for example Microthene™ FN510-00 (Equistar), silicone resin, polymethylsilsesquioxane silicone polymer, platelet shaped powder made from L-lauroyl lysine, and mixtures thereof.

The composition of the present invention further may comprise interference pigments, including hydrophobically-modified interference pigments. Herein, "interference pigments" means thin, platelike layered particles having two or more layers of controlled thickness. The layers have different refractive indices that yield a characteristic reflected color from the interference of typically two, but occasionally more, light reflections, from different layers of the platelike particle. One example of interference pigments are micas layered with about 50-300 nm films of $TiO_2$, $Fe_2O_3$, silica, tin oxide, and/or $Cr_2O_3$ and include pearlescent pigments. Interference pigments are available commercially from a wide variety of suppliers, for example, Rona (Timiron™ and Dichrona™), Presperse (Flonac™), Engelhard (Duochrome™), Kobo (SK-45-R and SK-45-G), BASE (Sicopearls™) and Eckart (Prestige™). In one embodiment, the average diameter of the longest side of the individual particles of interference pigments is less than about 75 microns; and alternatively less than about 50 microns.

According to a preferred embodiment, the shaving aid composition consists of:
a) 55 to 97% by weight of water,
b) 2 to less than 15% by weight of at least one oil,
c) 1 to 10% by weight of at least one shear thinning structurant, and
d) 0 to 20% by weight of at least one additive,
wherein the components a) to d) adding up to 100% by weight of the shaving aid composition.

According to another preferred embodiment, the shaving aid composition consists of:
a) 60 to 92% by weight of water,
b) 5 to 14% by weight of at least one oil,
c) 2 to 8% by weight of at least one shear thinning structurant, and
d) 0.5 to 18% by weight of at least one additive,
wherein the components a) to d) adding up to 100% by weight of the shaving aid composition.

It is preferred, that the hair removal device comprises at least one treatment sheet with aperture blades. The treatment sheet is preferably a planar sheet with aperture blades located within a cutting zone which is the treatment sheet surface that is exposed within the opening of the frame member. Alternatively, the hair removal device may comprise more than one treatment sheet, for example 2, 3, 6, 7 or 10. A hair removal device comprising 6 or 7 treatment sheets is preferred for geometrical reasons.

Moreover, a single treatment sheet has preferably a total aperture area A from 10 to 400 mm², more preferably from 20 to 200 mm² and even more preferably from 40 to 120 mm² and a total cutting zone area S preferably in the range from 100 to 800 mm², more preferably from 200 to 600 mm², and even more preferably from 250 to 480 mm² with the proviso that the transparency T=A/S is preferably in a range from 5 to 60%, more preferably from 10 to 50%, and even more preferably from 15 to 30%. It has been found that such a transparency supports the skin in an optimal way so that it bulges little into the apertures and maximizes the cutting length for an efficient shave.

It is preferred, that during shaving the skin contacting surface of the frame member or the cutting zone of the treatment sheet or both are in contact with the skin to be shaved.

Preferably, the treatment sheet is secured to the head with a frame member that has an opening to expose the surface of the treatment sheet, wherein the frame member is more preferably made from bendable non-corrosive metal, preferably aluminum or steel. According to a preferred embodiment, the surface of the frame member and/or the treatment sheet are hydrophobic or coated with PTFE. Preferably, the surface of the frame member and/or the treatment sheet has a polar component of the surface energy of 0.1 to 10 mJ/m², more preferably from 1 to 5 mJ/m².

To sum it up, the following aspects are the main advantages of the present invention:

The two-dimensional flat treatment sheets contain apertures with cutting edges and can therefore be used in all directions resulting in a more efficient shave.

The cutting edges within the apertures move parallel to the skin (the clearance angle is 0 degree) increasing the safety because they ride over unevenness on the skin surface.

The area around the apertures supports the skin reducing bulging ahead of the tip of the cutting blade which also increasing safety.

The pressure applied onto the skin is lower having the consequence that skin irritation is reduced.

If the lubricant is a moisturizer (preferred) if can be left on the skin after hair removal and does not need to be rinsed off The regimen can be used away from the bathroom.

The treatment sheet according to the present invention also has a considerably larger contact area giving rise to more friction between the device and the skin.

It is found that a user will apply the same force onto this treatment sheet than onto a conventional razor causing the resulting pressure on the skin to be much lower due to the large contact area of the treatment sheet and therefor a thicker fluid layer of the shaving aid can be maintained resulting in lower shear rates.

The present invention is further illustrated by the following figures and examples which show specific embodiments according to the present invention. However, these specific embodiments shall not be interpreted in any limiting way with respect to the present invention as described in the claims and in the general part of the specification.

BRIEF DESCRIPTION OF THE DRAWINGS

FIG. 7a is a diagram showing the rheology data regarding the storage modulus G' and the loss modulus G" of a first selected shaving aid composition, and FIG. 7b is a diagram showing the rheology data regarding the storage modulus G' and the loss modulus G" of a first selected shaving aid composition.

DETAILED DESCRIPTION OF THE INVENTION

Figure 1:
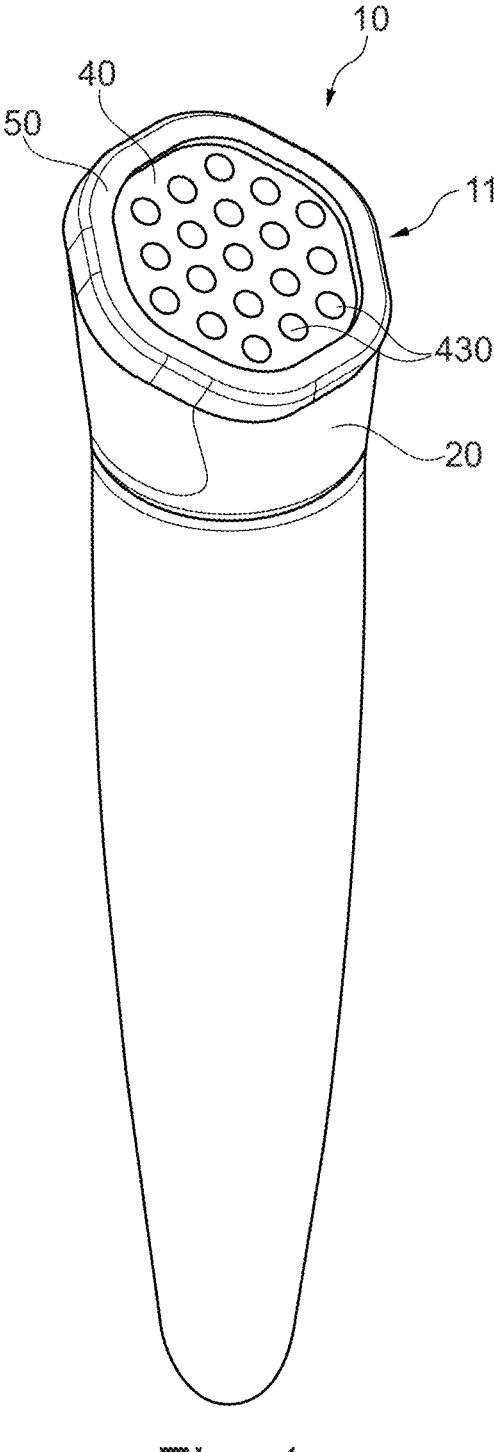
FIG. 1 is a perspective view of a hair removal device according to the present invention.

FIG. 1 is a perspective view of a hair removal device 10 having a head 11 and a handle 30. The head 11 comprising a housing 20 and a frame member 50 attached to the housing 20 and disposed over a treatment sheet 40 with a plurality of aperture blades 430. In this example the treatment sheet 40 and frame member 50 have a hexagonal shape. Other shapes are included in the present invention as shown in FIG. 5 below.

Figure 2:
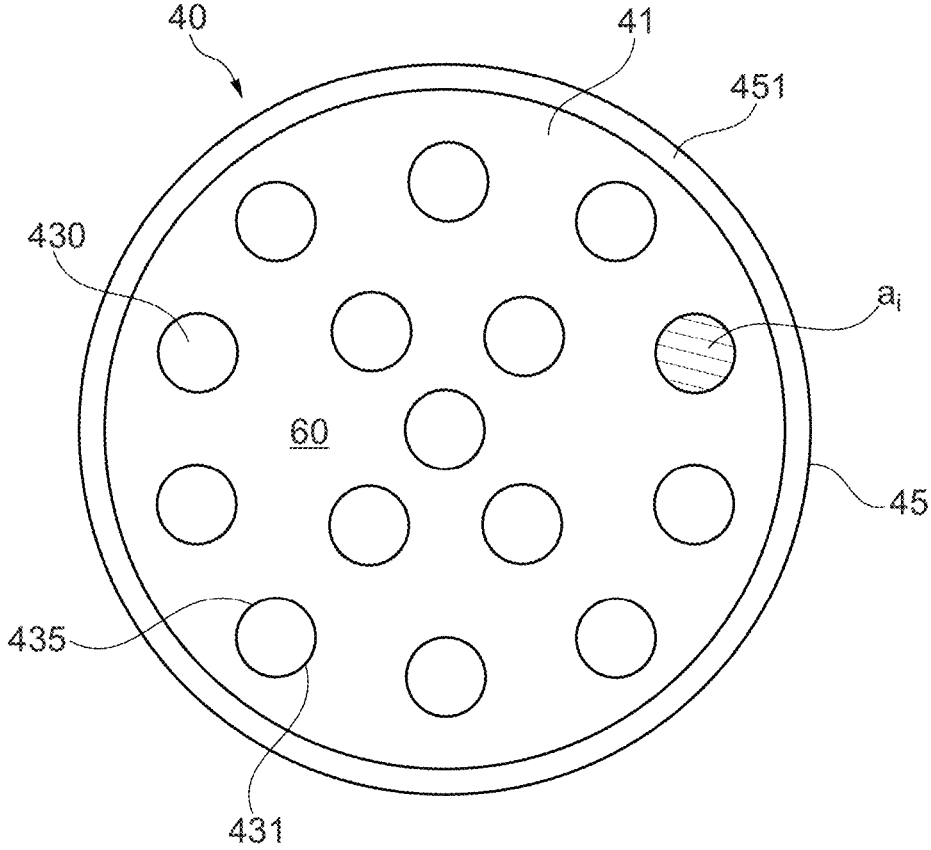
FIG. 2 is a top view of a treatment sheet in accordance with the present invention.

FIG. 2 shows a circular treatment sheet 40 of the present invention in a top view looking onto the skin contacting surface 41. The treatment sheet 40 comprises aperture blades 430 having a aperture perimeter 431 enclosing the aperture area $a_i$. The cutting edges 435 are shaped along at least a portion of the aperture perimeter 431 located at the skin contacting surface 41 resulting in an enclosed cutting edge.

In the hair removal device 10, the frame member 50 is disposed over the treatment sheet and covers the perimeter zone 451 on the skin contacting surface 41 and exposes the cutting zone 60 that is enclosed by the perimeter area 451, i.e., the cutting zone 60 is a portion of the skin contacting surface 41 that is visible when the frame member 50 is attached to the housing 20 of the head 11 of the hair removal device 10.

Figure 3:
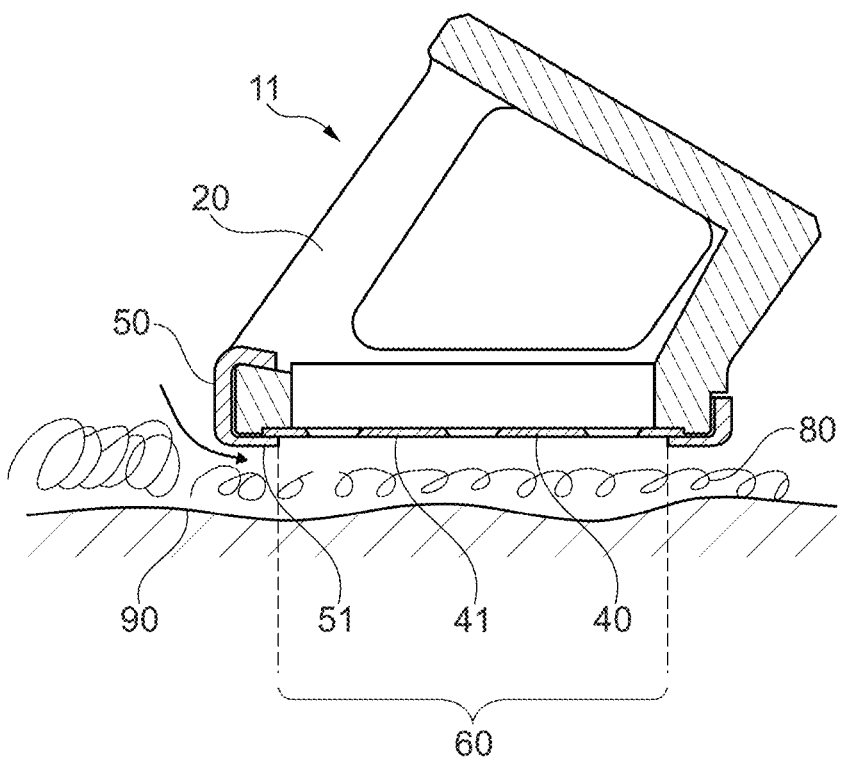
FIG. 3 is a cross-sectional view of a hair removal device in accordance with the present invention.

FIG. 3 is a cross-sectional view of a head 11 of a hair removal device in accordance with the present invention. The head 11 comprising a frame member 50 disposed over a treatment sheet 40. The treatment sheet 40 comprises a skin contacting surface 41 that is facing the skin surface 90 to be shaved. Similarly, the frame member 50 comprises a surface 51 that is facing the skin surface 90. A portion of the skin contacting surface 41 that is left exposed towards the skin surface 90 through an opening of the frame member 50 is referred to as the cutting zone 60. When used for removing hair from the skin surface 90, a layer of shaving aid 80 flows between the skin surface 90 and the skin facing surfaces 41 and 51 of the hair removal device 10.

Figure 4:
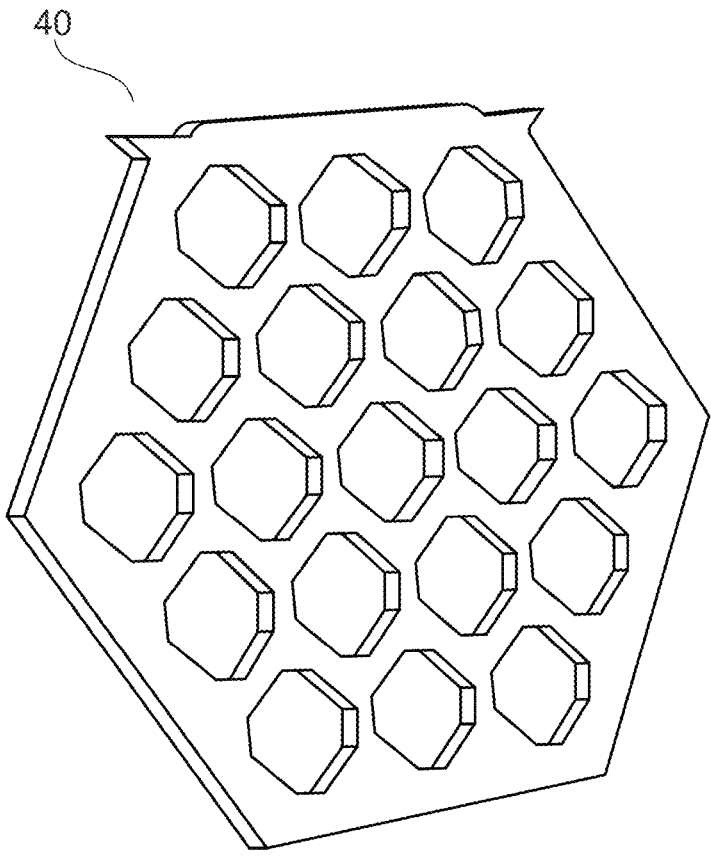
FIG. 4 is a top view onto the second surface of a treatment sheet in accordance with the present invention.
Figure 5A:
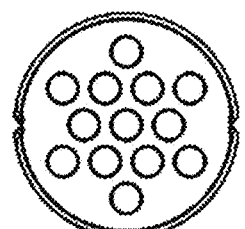
FIG. 5a-d are top views onto the second surface of alternative treatment sheets having different shapes in accordance with the present invention.
Figure 5B:
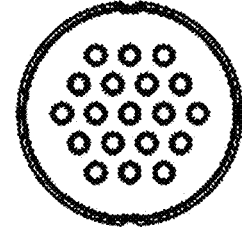
Figure 5C:
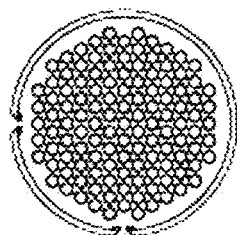
Figure 5D:
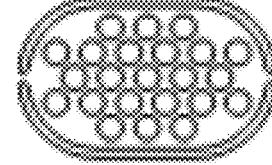

FIG. 4 shows a perspective view of a preferred hexagonal treatment sheet 40 according to the present invention with alternative number and arrangements of octagonal apertures. FIGS. 5a to 5d shows further top views of the first surface of treatment sheets according to the present invention with alternative number and arrangements of circular apertures. Consumer Tests To assess which shaving aid formulations are preferred in use and which ones are unsuitable, several shaving aid fluids were formulated and assessed during use of the hair removal device shown in FIG. 1. The shaving aids were assessed using the method according to the present invention involving the steps of applying the shaving aid to the skin to be shaved and subsequently removing hair from the skin using the hair removal device shown in FIG. 1. This method was carried out applying the shaving aid directly to dry skin and repeated applying the shaving aid to moist skin after washing the skin prior to using the method according to the present invention.

The performance of the method was assessed by the test candidates on a five-point scale (5=very good, 1=poor) for several shaving attributes including the overall performance of the shave, closeness of the shave, hair removal efficiency, lubrication during the shave, comfort, and safety of the shave. Shaving aids that are preferred reached an average score greater than 3, while unsuitable shaving aids received an average score of 3 or below.

The relative content of water, oil and structurants of the different shaving aid fluids that were tested are given in Table 1. The fluids A to C were rated higher than 3 for overall performance of the shave and are therefore preferred for the method of the current invention Shaving aid fluids D to E were rated 3 or below for overall performance of the shave and are therefore not suitable for the method of the current invention.

TABLE 1

| Shaving aid | Water % | Oil % | Structurant % | Additives % |
|---|---|---|---|---|
| A | 73 | 11 | 2 | 14 |
| B | 87 | 2 | 7 | 4 |
| C | 73 | 6 | 3 | 18 |

TABLE 1-continued

| Shaving aid | Water % | Oil % | Structurant % | Additives % |
|---|---|---|---|---|
| D | 77 | 2 | 0.5 | 19.5 |
| E | 91 | 0 | 0 | 9 |
| F | 69 | 0 | 0 | 31 |

The shaving aids have been prepared by the following methods:

Formula A:
1. In pot A, add water and heat to 75° C.
2. Add surfactants, chelants, polymers and humectants.
3. In pot B, add oils and fatty alcohols and heat to 75° C.
4. Add pot B to pot A and homogenise
5. Neutralise with Sodium hydroxide
6. Cool to 40° C.
7. Add preservatives, perfume and vitamin.

Formula B:
1. In pot A, add water and heat to 75° C.
2. Add surfactants, fatty alcohols, chelants, polymers and humectants.
3. In pot B add oils and heat to 75° C.
4. Add pot B to pot A and homogenise.
5. Cool to 40° C.
6. Add preservatives and perfume.

Formula C:
1 In pot A, add water and heat to 75° C.
2. Add chelants and humectants 3. In pot B, mix surfactants oils and fatty alcohols and heat to 75° C.
4. Add pot B to pot A and homogenise
5. Cool to 40° C.
6. Add preservatives, silicones, starches, perfume and vitamin.

Formula D:
1. In pot, mix water, polymers and sorbitol, then heat to 60° C.
2. Add surfactants, heat to 80° C.
3. Add TEA
4. Cool to 40° C.
5. Add oils, glycerin, preservatives and perfume
6. Concentrate combined with blowing agents and packed.

Formula E:
1. In pot, mix water and hydroxyethyl cellulose then heat to 75° C.
2. Add surfactants, chelants, polymers and humectants
3. Cool to 40° C. Add preservatives and perfume.

Formula F:
1. In pot, add water and heat to 75° C.
2. Add surfactants, chelants, polymers and humectants.
3. Cool to 40° C. Add preservatives and perfume and vitamin.

A detailed list of the ingredients of the shaving aids that were tested are given in Table 2.

TABLE 2

| | ingredient | A | B | C | D | E | F |
|---|---|---|---|---|---|---|---|
| water | water | 72.9 | 86.4 | 72.5 | 76.9 | 91.4 | 69.3 |
| oil | iso-hexadecane | | | 3.0 | | | |
| | iso-propyl iso-stearate | | | 1.3 | | | |
| | iso-propyl palmitate | 7.5 | | | | | |
| | dimethicone | 1.0 | 1.5 | 1.0 | | | |
| | amodimethicone | | 0.5 | | | | |
| | petrolatum | 1.6 | | | | | |
| | mineral oil | 0.88 | | | | | |
| | glyceryl oleate | | | | 1.8 | | |
| structurant | bethenyl alc. | | 0.4 | 0.60 | | | |
| | cetyl alc. | 0.88 | 1.0 | 0.90 | | | |
| | stearyl acl. | 0.88 | 2.9 | 1.1 | | | |
| | sodium polyacrylate | 0.12 | | 0.40 | | | |
| | starch | | | | | | |
| | carbomer | 0.16 | | | | | |
| | hydroxyethylcellulose | | | | | 0.5 | |
| | behentrimonium methosulfate | | 3.0 | | | | |
| additive | isopentane | | | | 2.5 | | |
| | isobutane | | | | 0.8 | | |
| | disodium EDTA | 0.05 | 0.13 | | | 0.1 | 0.12 |
| | Steareth 2 | 0.25 | | | | | |
| | Steareth 21 | 0.5 | | | | | |
| | polyquaternium | | | | | | 0.25 |
| | cetyl betaine | 4.4 | | | 1.0 | | |
| | glycerin | 4.0 | 3.0 | 7.1 | 1.0 | | 2.0 |
| | hexanediol | 0.80 | 1.17 | 0.80 | | | |
| | PEG-200 | | | 0.10 | | | 4.7 |
| | PEG-90M | | | | 0.10 | | |
| | sorbitol | | | | 0.68 | | 2.9 |
| | decyl glucoside | 0.48 | | | | | |
| | parfume | 0.30 | | 0.20 | 0.01 | | 0.20 |
| | tapioca starch | | | 5.0 | | | |
| | citric acid | | 0.03 | | | | 0.6 |
| | sodium hydroxide | 0.21 | | | | | |
| | preservatives | 0.48 | | 0.38 | 0.05 | 0.48 | |
| | hexylene glycol | | | | | 6.0 | |
| | myristic Acid | | | | 0.06 | | |
| | palmetic acid | | | | 9.2 | | |

TABLE 2-continued

| ingredient | A | B | C | D | E | F |
|---|---|---|---|---|---|---|
| stearic acid | 0.11 | | 0.10 | 1.3 | | |
| sodium lauryl sulfate | 2.4 | | | | | |
| sodium lauroamphoacetate | | | | | | 9.7 |
| sodium lauroyl sarcosinate | | | | | | 5.0 |
| sodium trideceth sulfate | | | | | | 5.0 |
| vitamin | 0.10 | | 5.5 | | | 0.25 |

Figures 6A, 6B, 6C:
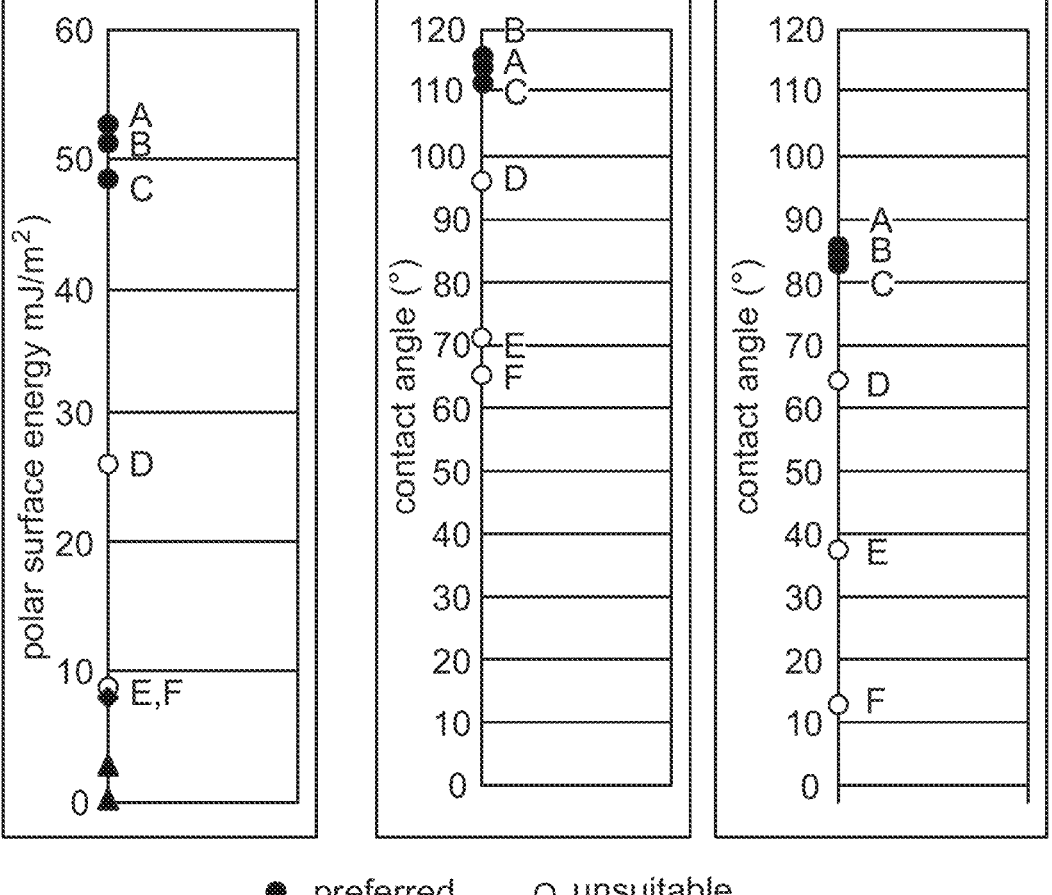
FIG. 6a is a diagram showing the surface energy data regarding the contact angle and the polar surface energy component of a first selected shaving aid composition.
FIG. 6b is a diagram showing the surface energy data regarding the contact angle and the polar surface energy component of a second selected shaving aid composition.
FIG. 6c is a diagram showing the surface energy data regarding the contact angle and the polar surface energy component of a third selected shaving aid composition.

FIGS. 6a to 6c are diagrams that illustrate the surface property data of selected shaving aids that were tested in use. Solid black circles represent shaving aids that were preferred in use over shaving aids that were found unsuitable in use represented by open circles. FIG. 6a shows the polar component to the surface free energy in milli Joule per meter squared for preferred and unsuitable shaving aids and also for skin (diamond symbol) and for surfaces of solid materials of the hair removal device (crosses).

Shaving aid D represents a typical shaving aid used with conventional hair removal devices that contains a plurality of straight linear blades. Shaving aid D was not liked when used with the shaving device of the present invention containing a treatment sheet with a plurality of cutting apertures. For the method of the present invention, shaving aid D was too thin and did not provide sufficient lubrication and cushioning between the skin and treatment sheet surfaces. This is because for shaving aid D, as can be seen from FIG. 6, the polar component of surface energy and the contact angles of the shaving aid on the surfaces of the device and the skin were too low compared to the preferred shaving aids. The higher polar component of surface energy and contact angles of the preferred shaving aids are required to form fluid droplets between the shaver and skin surface, which generate the required ball bearing-like lubrication mechanism and a cushioning layer of the shaving aid composition between the 2 surfaces.

It can clearly be seen that preferred shaving aids have a polar component to the surface free energy greater than about 40 mJ/m2. FIG. 6b shows the contact angle in degrees for preferred and unsuitable shaving aids when deposited on the treatment sheet of the hair removal device. It can clearly be seen that preferred shaving aids have a contact angle on the surface of the treatment sheet greater than about 100°. FIG. 6c shows the contact angle in degrees for preferred and unsuitable shaving aids when deposited on skin of the hair removal device. It can clearly be seen that preferred shaving aids have a contact angle on the skin surface greater than about 80°.

FIGS. 7a and 7b are diagrams that illustrate the rheology properties of selected shaving aids that were tested in use. Solid black circles represent shaving aids that were preferred in use over shaving aids that were found unsuitable in use represented by open circles. FIG. 7a shows the storage modulus G' measured in Pascal for preferred and unsuitable shaving aids. FIG. 7b shows the loss modulus G' measured in Pascal for preferred and unsuitable shaving aids.

Shaving aid D represents a typical shaving aid used with conventional hair removal devices that contain a plurality of straight linear blades. Shaving aid D was not liked when used with the shaving device of the present invention containing a treatment sheet with a plurality of cutting apertures. For the method of the present invention, shaving aid D was too thin and did not provide sufficient lubrication and cushioning between the skin and treatment sheet surfaces. This is because for shaving aid D, as can be seen from FIG. 7, the storage and loss modulus are too low compared to the preferred shaving aids. The higher storage and loss modulus of the preferred shaving aids are required to form a cushioning layer of the shaving aid composition between the device surface and the skin surface.

It can clearly be seen that preferred shaving aids have a storage modulus greater than about 150 Pascal. It can clearly be seen that preferred shaving aids have a loss modulus greater than about 50 Pascal.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" or ±10% of the disclosed dimension.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for removing hair from an area of skin, comprising the step of:
   (A) applying a shaving aid composition to the area of skin to be shaved, the shaving aid composition comprising
      (a) 55 to 97% by weight of water,
      (b) 2 to less than 15% by weight of at least one oil,
      (c) 1 to 10% by weight of at least one shear thinning structurant, and
      (d) 0 to 20% by weight of at least one additive,
         wherein the shaving aid composition has a polar component of surface free energy of 30 to 80 $mJ/m^2$ and wherein the components (a) to (d) add up to 100% by weight of the shaving aid composition,
   (B) shaving the area of skin to be shaved using a hair removal device comprising at least one treatment sheet with aperture blades.

2. The method of claim 1, wherein the shaving aid composition has a polar component of surface free energy of 40 to 60 mJ/m$^2$.

3. The method of claim 1, wherein the shaving aid composition has a storage modulus G' of 150 to 1500 Pa.

4. The method of claim 1, wherein the shaving aid composition has a contact angle on the surface of the at least one treatment sheet of 100 to 180°.

5. The method of claim 1, wherein the at least one oil is selected from the group consisting of:

hydrocarbons, esters, amides, others, silicones, and mixtures thereof.

6. The method of claim 1, wherein the at least one shear thinning structurant is selected from the group consisting of clays, gums, microgels, super absorbent polymers, gel networks formed from fatty amphiphiles and mixtures thereof.

7. The method of claim 1, wherein the at least one additive is selected from the group consisting of emulsifiers, skin care actives, moisturizing agents, conditioning agents, exfoliating agents, antimicrobial agents, antidandruff agents, skin lightening agents (sunless) tanning agents, perfumes, preservatives, chelants, sensates, desquamation actives, anti-acne actives, topical anaesthetics, tanning actives, antimicrobial actives, sunscreen actives, visual skin enhancers minerals, opacifiers, anti-inflammatories, antioxidants, minerals, anti-inflammatories, antioxidants, humectants, particles and mixtures thereof.

8. The method of claim 1, wherein the shaving aid composition consists of:

a) 60 to 92% by weight of the water, b) 5 to 14% by weight of the at least one oil, c) 2 to 8% by weight of the at least one shear thinning structurant, and d) 1 to 18% by weight of the at least one additive, the components a) to d) adding up to 100% by weight of the shaving aid composition.

9. The method of claim 1, wherein the at least one treatment sheet is secured to a head with a frame member that has an opening to expose a cutting zone of the at least one treatment sheet, wherein the frame member is made from bendable non-corrosive metal, preferably aluminum or steel.

10. The method of claim 1, wherein the at least one treatment sheet is a planar sheet with aperture blades located within a cutting zone.

11. The method of claim 1, wherein the at least one treatment sheet has a total aperture area A from 10 to 400 mm$^2$ and a cutting zone area S in the range from 100 to 800 mm$^2$ and a transparency T=A/S is in a range from 5 to 60%.

12. The method of claim 11, wherein during shaving a skin contacting surface of a frame member or a cutting zone of the at least one treatment sheet or both are in contact with the skin to be shaved.

13. The method of claim 1, wherein a surface of a frame member and/or the at least one treatment sheet are hydrophobic or coated with PTFE, having a polar component of the surface energy of 0 to 10 mJ/m$^2$.

14. The method of claim 1, wherein the hair removal device comprises 2,3,6,7 or 10 treatment sheets.

* * * * *